United States Patent
Myint et al.

(10) Patent No.: US 12,171,953 B2
(45) Date of Patent: Dec. 24, 2024

(54) CATHETER HAVING A LAMINATED POLYTETRAFLUOROETHYLENE LINER AND METHOD OF MANUFACTURE

(71) Applicant: Creganna Unlimited Company, Galway (IE)

(72) Inventors: Khin Myint, Plymouth, MN (US); Sandra Patras, Greenfield, MN (US); Robert Garryl Hudgins, Monticello, MN (US)

(73) Assignee: Creganna Unlimited Company, Galway (IE)

( * ) Notice: Subject to any disclaimer, the term of this patent is extended or adjusted under 35 U.S.C. 154(b) by 0 days.

(21) Appl. No.: 17/873,636

(22) Filed: Jul. 26, 2022

(65) Prior Publication Data
US 2024/0033467 A1    Feb. 1, 2024

(51) Int. Cl.
*A61M 25/00* (2006.01)
*C08L 27/18* (2006.01)

(52) U.S. Cl.
CPC ......... *A61M 25/0009* (2013.01); *C08L 27/18* (2013.01); *A61M 25/0045* (2013.01)

(58) Field of Classification Search
CPC ...... A61M 2025/0047; A61M 25/0009; A61M 25/0045; A61L 2420/02; A61L 29/085; C08L 27/18; B29L 2031/7542; B29K 2627/18
USPC .................................................. 604/264, 523
See application file for complete search history.

(56) References Cited

U.S. PATENT DOCUMENTS

| | | | | |
|---|---|---|---|---|
| 4,301,803 A | * | 11/1981 | Handa | A61M 25/1029 604/103 |
| 2004/0225278 A1 | * | 11/2004 | Poole | A61M 25/0051 604/529 |
| 2006/0058867 A1 | * | 3/2006 | Thistle | A61L 27/507 623/1.53 |
| 2007/0095473 A1 | | 5/2007 | Farnsworth et al. | |
| 2015/0320971 A1 | | 11/2015 | Leeflang et al. | |
| 2019/0118456 A1 | * | 4/2019 | Lindsey | B32B 37/182 |
| 2020/0069927 A1 | * | 3/2020 | Malek | A61M 27/006 |
| 2020/0306501 A1 | * | 10/2020 | Yee | A61M 25/0013 |
| 2023/0364393 A1 | * | 11/2023 | Rajaram | A61M 25/0023 |

FOREIGN PATENT DOCUMENTS

| | | | | |
|---|---|---|---|---|
| CN | 106893068 A | * | 6/2017 | C08G 18/12 |
| WO | WO-2006124437 A1 | * | 11/2006 | C09J 5/02 |
| WO | 2010027662 A1 | | 3/2010 | |
| WO | WO-2010068793 A1 | * | 6/2010 | A61M 25/0009 |

OTHER PUBLICATIONS

International Search Report for International Application No. PCT/IB2023/057508 dated Feb. 5, 2024.

* cited by examiner

*Primary Examiner* — Yan Lan

(57) ABSTRACT

A catheter and a method of making a device having an outer member, a primer, and an inner liner laminated to the outer member. The primer is provided between the outer member and the inner liner and annealed to secure the inner liner to the outer member.

10 Claims, 2 Drawing Sheets

CATHETER HAVING A LAMINATED POLYTETRAFLUOROETHYLENE LINER AND METHOD OF MANUFACTURE

FIELD OF THE INVENTION

The present invention relates to a method and a polytetrafluoroethylene (PTFE) liner which is laminated onto a metal surface using a primer solution. In particular, the invention relates to securing a polytetrafluoroethylene liner to a metal tube to form a catheter.

BACKGROUND OF THE INVENTION

Vascular therapy uses minimally invasive, catheter-based procedures and specialized equipment and techniques. Catheters used in these procedures commonly employ a coating or liner on the inner wall to provide a smooth inner surface. A smooth inner diameter (ID) associated with these devices is beneficial in reducing friction as devices, such as, stents, balloons, atherectomy or thrombectomy are pushed through the catheter lumen. If the internal diameter (ID) of the catheter is not of sufficient lubricity, the devices may cause damage to the liner as the devices are pushed through the catheter lumen. The effect of increased lubricity of the catheter ID is a reduced deployment force of catheter devices as they are passed through the lumen, increasing the likelihood of a successful procedure.

The mechanical properties of a catheter liner are also important. For example, high tensile and yield strength may be required when certain devices are passed through catheters in a compressed state. The compressed state exerts an outward radial force, which causes friction with the ID, commonly making delivery of the device therethrough difficult. On the other hand, high flexibility of a liner is often desirable when catheters must pass through vasculature that involves sharp twists and turns. In this situation, a highly flexible liner with intermediate tensile strength is often more desirable than a high tensile liner with low flexibility/high rigidity.

Various materials have been pursued as inner wall (base liner) materials for use. One material that has been considered is polytetrafluoroethylene (PTFE). Polytetrafluoroethylene is beneficial as it has a number of beneficial properties, including excellent chemical resistance, high temperature resistance, biocompatibility and very low coefficient of friction/high lubricity.

Known polytetrafluoroethylene-based materials for use within catheter applications suffer from various drawbacks. For example, certain extruded polytetrafluoroethylene tubes can be produced with sufficiently thin walls and sufficiently high tensile strengths, but exhibit high rigidities and high tensile modulus values, rendering them unsuitable. In addition, modified extruded polytetrafluoroethylene tubes have been reported with high tensile strength, but undesirable stiffness, due to the method by which the high tensile strength was obtained. Alternatively, dip-coated tubes typically have relatively low abrasion resistance, and, as such, the ID of these tubes often has inferior lubricity properties.

It would be beneficial to provide a polytetrafluoroethylene liner for use in a metal or stiff tube which provides the strength and lubricity characteristics required. It would also be beneficial to provide a method of laminating the polytetrafluoroethylene liner to the metal tube.

SUMMARY OF THE INVENTION

An object is to provide a metal plate or tubing with a polytetrafluoroethylene liner which is laminated thereto to allow metal plate or tubing to be flexed or bent without the delamination of the polytetrafluoroethylene liner.

An object is to provide a method of manufacturing a catheter which ensures that a polytetrafluoroethylene liner will remain laminated to a metal plate or tubing as the metal plate or tubing is flexed or bent.

An object is to provide a catheter with a polytetrafluoroethylene liner laminated to a metal tube which allows the catheter to bend or flex without the delamination of the polytetrafluoroethylene liner.

An embodiment is directed to a catheter having an outer member, a primer, and an inner liner laminated to the outer member. The primer is provided between the outer member and the inner liner and annealed to secure the inner liner to the outer member.

An embodiment is directed to a method of laminating a polytetrafluoroethylene liner to a flexible outer member. The method includes: applying a primer to an outer surface of the polytetrafluoroethylene liner; applying the primer to an inner surface of the outer member, the inner surface of the outer member facing the outer surface of the polytetrafluoroethylene liner; annealing the primer on the outer surface and the primer on the inner surface; reapplying the primer to the outer surface and the inner surface; moving the outer surface and the inner surface into engagement with each other; applying a force to maintain the engagement of the outer surface with the inner surface; and annealing the reapplied primer to laminate the outer surface to the inner surface.

Other features and advantages of the present invention will be apparent from the following more detailed description of the illustrative embodiment, taken in conjunction with the accompanying drawings which illustrate, by way of example, the principles of the invention.

DETAILED DESCRIPTION OF THE INVENTION

Figure 1:
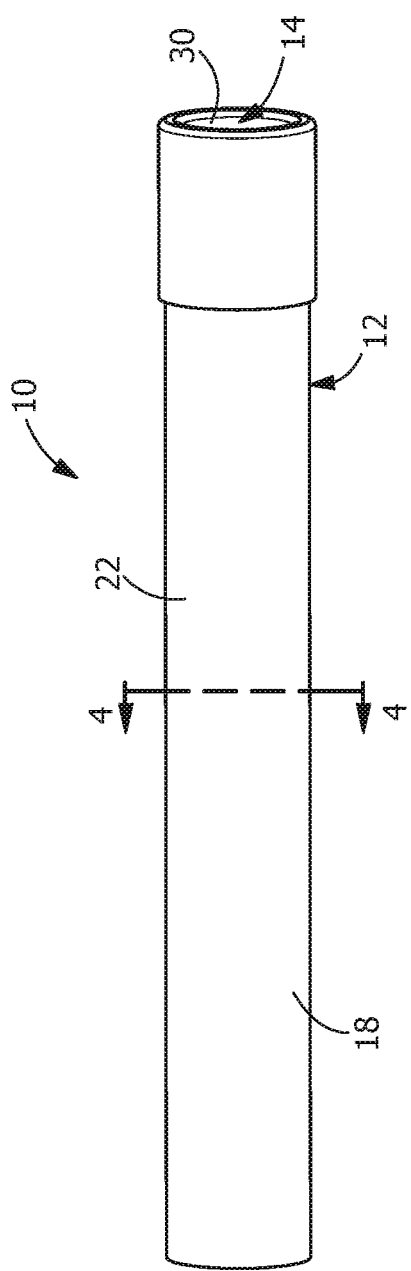
FIG. 1 is a perspective view of an illustrative embodiment of a catheter of the present invention.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise.

Figure 2:
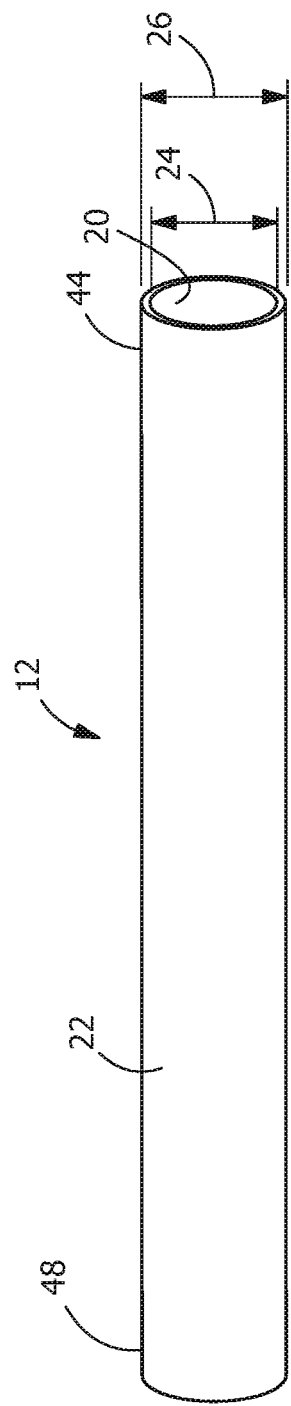
FIG. 2 is a perspective view of an illustrative embodiment of an outer member of the catheter of FIG. 1.
Figure 3:
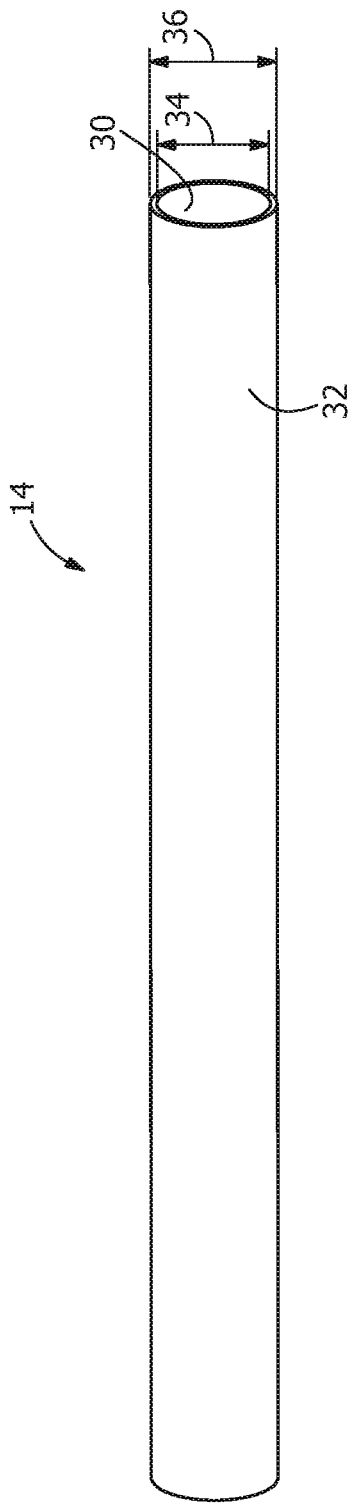
FIG. 3 is a perspective view of an illustrative embodiment of an inner liner of the catheter of FIG. 1.
Figure 4:
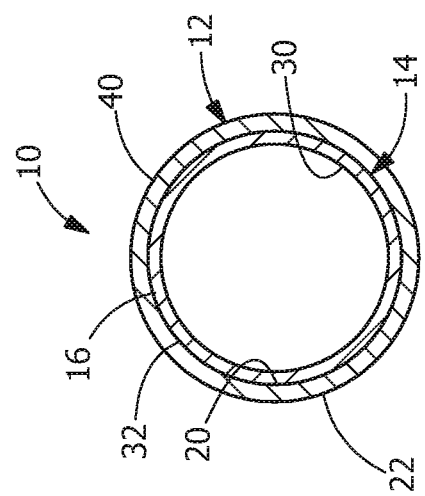
FIG. 4 is an enlarged cross sectional view taken along line 4-4 of FIG. 1.

As shown in FIGS. 1 to 4, a device 10 has an outer flexible member 12 and an inner liner 14. The outer flexible member 12 and the inner liner 14 are secured to each other by a primer 16 positioned between the outer flexible member 12 and the liner 14, as shown in FIG. 4. In the illustrative embodiment shown, the outer flexible member 12 and the inner liner 14 are tubular members with circular cross-sectional areas, wherein the device 10 is a catheter 18. However, the outer flexible member 12 and the inner liner 14 may have other configurations, including, but not limited to planar configurations.

In the illustrative embodiment shown in FIG. 2, the outer flexible member 12 is a hollow flexible metal member with an inner wall 20 and an outer wall 22. In the illustrative embodiment shown, the inner wall 20 and the outer wall 22 are solid, continuous metal surfaces and are not made of mesh or other perforated material. The outer flexible member 12 has an inner diameter 24 and an outer diameter 26. The outer flexible member 12 may be, but is not limited to, a laser cut hypotube. In illustrative embodiments, the outer member 12 of a catheter 18 has an inner diameter 24 of between approximately 1 mm to approximately 13 mm, an outer diameter 26 of between approximately 1.12 mm to approximately 15 mm, and a thickness of between approximately 0.06 mm to approximately 1 mm.

In the illustrative embodiment shown in FIG. 3, the inner liner 14 is a hollow flexible liner tube or member with an inner wall 30 and an outer wall 32. In the illustrative embodiment shown, the inner wall 30 and the outer wall 32 are solid, continuous surfaces and are not made of mesh or other perforated material. The inner liner 14 has an inner diameter 34 and an outer diameter 36. The inner liner 14 may be made of, but is not limited to, polytetrafluoroethylene (PTFE). The inner liner 14 has a high lubricity or a low coefficient of friction, which allows ease of deployment of medical devices (not shown) through the inner liner 14 and the catheter 18. The inner liner 14 also has sufficiently high tensile strength to avoid puncture or tearing of the inner liner 14 as the medical devices are moved therethrough. In illustrative embodiments, the inner liner 14 of a catheter 18 has an inner diameter 34 of between approximately 0.8 mm to approximately 12.7 mm, and outer diameter 36 of between approximately 1 mm to approximately 13 mm, and a thickness of between approximately 0.1 mm to approximately 0.15 mm.

The primer 16 is a mixture which provides sufficient adhesion between the outer wall 32 of the inner liner 14 and the inner wall 20 of the outer member 12. In the illustrative embodiment, the primer 16 of a catheter 18 has a thickness of between approximately 0.012 mm to approximately 0.1 mm.

In one illustrative embodiment, the primer 16 includes the following:

| Description | % By Volume |
| --- | --- |
| Ethanol | 20-30 |
| Sterile Water | 15-25 |
| Dimethylacetamide (DMAC) | 1-5 |
| Triethylamine based solution | 35-65 |
| Polyfunctional Aziridine Crosslinker | 1-5 |

An example of the triethylamine based solution is Primer 5-017 supplied by Coatings2Go. An example of the polyfunctional aziridine crosslinker is Crosslinker A supplied by Coatings2Go.

The dimethylacetamide in the primer allows for better control of the viscosity of the primer 16. In addition, as the primer 16 is reactive and changes over time, the dimethylacetamide allows for a longer effective pot or shelf life of the primer 16.

When mixing the primer 16 a new syringe to draw each liquid from its container or a properly cleaned and labeled beaker should be used to prevent cross contamination.

In an illustrative embodiment, when mixing the primer, the ethanol is first added, followed in order by the sterile water, the dimethylacetamide, the triethylamine based solution, and the polyfunctional aziridine crosslinker. The triethylamine based solution and the polyfunctional aziridine crosslinker are slowly or gradually added to the mixture. The mixture is covered and allowed to mix or stir for approximately 5 to approximately 7 minutes.

Prior to applying the primer 16 to the outer member 12 and the inner liner 14, the surfaces of the outer member 12 and the inner liner 14 must be properly cleaned to remove any loose or oily residue that may prevent bonding, or which may allow the inner liner 14 to easily separate from the outer member 12 resulting in delamination. In order to ensure removal all residue, a combination of detergent, polar, and non-polar solvents is used.

The outer member 12 and the inner liner 14 are placed in a cleaning mixture. An illustrative embodiment of the cleaning mixture includes a 1% solution of sterile water and Alconox Powdered Precision Cleaner mixed with water. The outer member 12 and the inner liner 14 and the cleaning mixture may be cleaned using an ultrasonic cleaner. Upon completion of the cleaning cycle, the outer member 12 and the inner liner 14 are exposed to a sterile water rinse, an acetone soak, and an alcohol soak. Alternatively, the inner liner 14 may be cleaned with a 70% to 99% solution of isopropyl alcohol (IPA).

With the outer member 12 and the liner 14 properly cleaned and the primer 16 properly mixed, the polytetrafluoroethylene liner is first precoated. In the illustrative embodiment, the liner 14 is cut to approximately 47 inches to approximately 49 inches in length, with a preferred length of approximately 48 inches. The liner 14 is placed onto a primer precoating mandrel. The outside wall 32 of the liner 14 may then be cleaned with a 99% isopropyl alcohol damp cloth along its entire length. The liner 14 with the primer precoating mandrel is allowed to dry with the distal end 42 up for approximately 5 seconds to approximately 25 seconds, with a preferred time of approximately 15 seconds.

A super-absorbent foam pad is wetted with the primer 16. A thin coat of primer 16 is then applied to the outer wall 32 of the liner 14. The coated liner 14 is then air dried for approximately 8 minutes to approximately 12 minutes, with a preferred time of approximately 10 minutes. These steps are repeated.

The twice pre-coated liner 14 is then annealed in an oven for approximately 5 minutes to approximately 7 minutes, with a preferred time of approximately 6 minutes, at approximately 155° F. to approximately 165° F., with a preferred temperature of approximately 160° F. Once completed, the liner 14 is removed from the oven to cool down in a clean room until reaching room temperature.

The distal end 44 of the outer member 12 is also precoated. The primer 16 is applied to the distal end 44 to a depth of approximately 3 inches. The inner wall 20 of the outer member 12 is also wiped from the distal end 44 to smooth out and remove excess primer 16. The outer member 12 is allowed to dry with the distal end 44 up for approximately 10 minutes +/−1 minutes. These steps are repeated.

The twice pre-coated outer member 12 is then annealed in an oven for 6 minutes +/−1 minutes for 160° F.+/−5° F. Once completed, the outer member 12 is removed from the oven to cool down in a clean room until reaching room temperature.

With the inner liner 14 and the outer member 12 pre-coated, the catheter 18 is assembled. A liner pull wire in inserted into the distal end 44 of the outer member 12 and pulled until the pull wire comes out from a proximal end 48 of the outer member 12. The outer member 12 is positioned and retained in a fixture in which the proximal end 48 is exposed approximately 0.25 inches from the fixture 50.

A balloon or inflatable mandrel is positioned in the inner liner 14 and the inner liner 14 with the inflatable mandrel is positioned on a fixture assembly proximate the outer member. An end of the pull wire is tied to the end of the inner liner 14.

The inner liner 14 is pulled through the outer member 12. As this occurs, additional primer 16 is applied to the outer wall 32 of the inner liner 14.

With the inner liner 14 fully inserted into the outer member 12, the pull wire 46 is removed from the inner liner 14. The inflatable mandrel is inflated to apply force to the inner member 14, causing the outer wall 32 of the inner member 14 to be pushed against the inner wall 20 of the outer member 12. With the inflatable mandrel inflated, the primer 16 is applied to the outer wall 22 of the outside member 12 at approximately 0.25 inches of both the proximal end 48 and the distal end 44 of the outer member 12. Excess primer 16 is gently wiped along the entire outer wall 22 of the outside member 12.

The inner liner 14 and the outer member 12 with the inflatable mandrel inflated are maintained in position for a minimum of approximately 13 minutes to approximately 17 minutes, with a preferred time of approximately 15 minutes to allow the primer 16 to set. The inflatable mandrel is then deflated and removed from the inner liner 14.

A process or reflow mandrel is then inserted into the inner liner 14. The inner liner 14 and the outer member 12, with the process mandrel positioned therein, are moved into an oven which has been preheated to a temperature at 430° F. The temperature is set to 420° F. and the inner liner 14 and the outer member 12 are positioned in the oven for approximately 18 minutes to approximately 22 minutes, with a preferred time of approximately 20 minutes, to allow the primer 16 to anneal. Once completed, the catheter 18, with the inner liner 14 properly secured to the outer member 12 is removed from the oven to cool down in a clean room until reaching room temperature.

With the primer 16 properly annealed and the inner liner 14 secured to the outer member 12, any excess primer 16 is removed from the outer wall 22 of the outer member 12. The process mandrel is removed. The inner liner 14 is trimmed to allow the inner liner 14 to extend approximately 0.5 inches past the proximal end 48 of the outer member 12. The portion of the inner liner 14 which extends past the proximal end 48 is flared and folded over the proximal end 48, as shown in FIG. 1.

A catheter 18 made using the outer member 12, the inner liner 14 and the primer 16 allows for an optimal inner diameter 34 of the inner liner 14 while minimizing the outer diameter 26 of the outer member 12. The use of the primer 16 prevents the delamination of the inner liner 14 from the outer member 12 as the catheter is flexed or bent. The combination of the inner liner 14, with a high lubricity and high tensile strength, with the outer member 12, with proper flexibility and bending characteristics allows the catheter to be used for various medical devices or procedures, including, but not limited to, stents, balloons, atherectomy or thrombectomy.

While the invention has been described with reference to a preferred embodiment, it will be understood by those skilled in the art that various changes may be made, and equivalents may be substituted for elements thereof without departing from the spirit and scope of the invention as defined in the accompanying claims. One skilled in the art will appreciate that the invention may be used with many modifications of structure, arrangement, proportions, sizes, materials and components and otherwise used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims, and not limited to the foregoing description or embodiments.

The invention claimed is:

1. A catheter comprising:
an outer member having a pre-coated inner wall and a metal outer wall having a solid, continuous metal surface;
a primer containing dimethylacetamide;
an inner polytetrafluoroethylene liner having a pre-coated outer wall, the pre-coated outer wall of the inner polytetrafluoroethylene liner laminated to the pre-coated inner wall of the outer member;
wherein the primer is provided between the pre-coated inner wall of the outer member and the pre-coated outer wall of the inner polytetrafluoroethylene liner, the primer is annealed to secure the inner liner to the outer member.

2. The catheter as recited in claim 1, wherein an outer diameter of the outer member is between approximately 1.12 mm to approximately 15 mm.

3. The catheter as recited in claim 2, wherein outer member has a thickness of between approximately 0.06 mm to approximately 1 mm.

4. The catheter as recited in claim 1, wherein coating of the pre-coated outer wall of the inner polytetrafluoroethylene liner and coating of the pre-coated inner wall of the outer member is the same material as the primer.

5. The catheter as recited in claim 1, wherein an inner diameter of the inner liner is between approximately 0.8 mm to approximately 12.7 mm.

6. The catheter as recited in claim 5, wherein inner liner has a thickness of between approximately 0.1 mm to approximately 0.15 mm.

7. The catheter as recited in claim 1, wherein the primer has a thickness of between approximately 0.012 mm to approximately 0.1 mm.

8. A catheter comprising:
an outer member;
a primer, the primer has a thickness of between approximately 0.012 mm to approximately 0.1 mm, the primer includes dimethylacetamide, the dimethylacetamide is approximately 1% to approximately 5% of the total volume of the primer;
an inner liner laminated to the outer member;

wherein the primer is provided between the outer member and the inner liner and annealed to secure the inner liner to the outer member.

9. The catheter as recited in claim 8, wherein the primer includes a crosslinker.

10. A catheter comprising:
an outer member having a metal outer wall having a solid, continuous metal surface;
a primer, the primer including dimethylacetamide, the dimethylacetamide being approximately 1% to approximately 5% of the total volume of the primer;
an inner liner laminated to the outer member;
wherein the primer is provided between the outer member and the inner liner and annealed to secure the inner liner to the outer member.

\* \* \* \* \*